(12) United States Patent
Sutherland et al.

(10) Patent No.: US 9,002,159 B2
(45) Date of Patent: Apr. 7, 2015

(54) OPTICAL SWITCH

(75) Inventors: Ying Sutherland, Glasgow (GB);
Fraser William Havern Sutherland, Glasgow (GB); John Targell, Kilmarnock (GB)

(73) Assignee: CardioPrecision Ltd, Glasglow (GB)

( * ) Notice: Subject to any disclaimer, the term of this patent is extended or adjusted under 35 U.S.C. 154(b) by 0 days.

(21) Appl. No.: 13/825,235

(22) PCT Filed: Aug. 30, 2011

(86) PCT No.: PCT/GB2011/051618
§ 371 (c)(1),
(2), (4) Date: Apr. 17, 2013

(87) PCT Pub. No.: WO2012/038714
PCT Pub. Date: Mar. 29, 2012

(65) Prior Publication Data
US 2013/0202251 A1 Aug. 8, 2013

(30) Foreign Application Priority Data

Sep. 21, 2010 (GB) .................................. 1015746.9

(51) Int. Cl.
*G02B 6/35* (2006.01)
*A61B 1/00* (2006.01)
*A61B 5/00* (2006.01)
*A61B 17/02* (2006.01)
(Continued)

(52) U.S. Cl.
CPC .............. *G02B 6/35* (2013.01); *A61B 1/00126* (2013.01); *A61B 1/07* (2013.01); *A61B 5/00* (2013.01); *A61B 17/02* (2013.01); *A61B 19/5202* (2013.01); *A61B 2019/5206* (2013.01); *A61B 2562/0233* (2013.01); *G02B 6/3504* (2013.01); *G02B 6/3574* (2013.01)

(58) Field of Classification Search
USPC ....................................................... 385/16, 24
See application file for complete search history.

(56) References Cited

U.S. PATENT DOCUMENTS 4,091,612 A * 5/1978 Meisner et al. ................ 368/155
D248,870 S 8/1978 Hass
(Continued)

FOREIGN PATENT DOCUMENTS

DE 19629304 A1 1/1998
DE 202004001136 U1 4/2004
(Continued)

OTHER PUBLICATIONS

Jakober, F., "International Search Report" for PCT/GB2011/051618, as mailed Dec. 20, 2011, 3 pages.
(Continued)

*Primary Examiner* — Kaveh Kianni
(74) *Attorney, Agent, or Firm* — Winstead PC

(57) ABSTRACT

An optical switch (10) includes a light input (12*a*), a plurality of light outputs (12*b*) and at least one light pathway movable from a first position where a light communication path is formed between a light input (14*a*) and a first light output (14*b*) and a second position where a light communication path is formed between the light input and a plurality of light outputs. Multiple light pathways are configured within the switch and selectable by rotation of a switch housing part enabling sequential selection of light communication paths. The switch can be used on a surgical device to control illumination of the surgical field during a procedure.

26 Claims, 5 Drawing Sheets

(51) Int. Cl.
  *A61B 19/00* (2006.01)
  *A61B 1/07* (2006.01)

(56) References Cited

U.S. PATENT DOCUMENTS

| | | | |
|---|---|---|---|
| 4,616,633 A | 10/1986 | Vargas Garcia | |
| 4,702,230 A | 10/1987 | Pelta | |
| 5,200,939 A * | 4/1993 | Nishiwaki et al. | 369/44.12 |
| 5,634,883 A | 6/1997 | Chin et al. | |
| 5,676,636 A | 10/1997 | Chin | |
| 5,941,819 A | 8/1999 | Chin | |
| 5,967,971 A | 10/1999 | Bolser | |
| 6,015,378 A | 1/2000 | Borst et al. | |
| D433,134 S | 10/2000 | Pitesky | |
| 6,159,231 A | 12/2000 | Looney et al. | |
| 6,274,859 B1 * | 8/2001 | Yoshino et al. | 219/746 |
| 6,347,168 B1 * | 2/2002 | Shimomura et al. | 385/19 |
| 6,522,794 B1 * | 2/2003 | Bischel et al. | 385/4 |
| 6,965,710 B2 * | 11/2005 | Makio | 385/18 |
| D522,140 S | 5/2006 | Stalcup et al. | |
| D523,142 S | 6/2006 | Stalcup et al. | |
| 7,194,153 B1 * | 3/2007 | Yajima et al. | 385/18 |
| D568,471 S | 5/2008 | Engler | |
| D586,914 S | 2/2009 | DaSilva | |
| D589,145 S | 3/2009 | Miller | |
| D658,286 S | 4/2012 | Ryshkus et al. | |
| D669,171 S | 10/2012 | Boedeker | |
| 2001/0009971 A1 | 7/2001 | Sherts et al. | |
| 2003/0053744 A1 * | 3/2003 | Makio | 385/18 |
| 2003/0060686 A1 | 3/2003 | Taylor et al. | |
| 2004/0242968 A1 | 12/2004 | Hill et al. | |
| 2004/0260366 A1 | 12/2004 | Svanberg et al. | |
| 2005/0041909 A1 * | 2/2005 | Nakano et al. | 385/16 |
| 2005/0092333 A1 | 5/2005 | Cosgrove | |
| 2005/0119530 A1 | 6/2005 | Douglas et al. | |
| 2005/0159650 A1 * | 7/2005 | Raymond et al. | 600/201 |
| 2006/0217596 A1 | 9/2006 | Williams | |
| 2006/0217597 A1 | 9/2006 | Vayser et al. | |
| 2007/0112256 A1 * | 5/2007 | Terakawa et al. | 600/178 |
| 2007/0129608 A1 | 6/2007 | Sandhu | |
| 2007/0238932 A1 | 10/2007 | Jones et al. | |
| 2008/0002426 A1 | 1/2008 | Vayser et al. | |
| 2009/0244905 A1 * | 10/2009 | Ishida et al. | 362/311.06 |
| 2010/0312069 A1 | 12/2010 | Sutherland et al. | |
| 2012/0154912 A1 * | 6/2012 | Shihoh | 359/554 |
| 2013/0155723 A1 * | 6/2013 | Coleman | 362/621 |
| 2013/0267785 A1 * | 10/2013 | Sutherland et al. | 600/202 |
| 2014/0128141 A1 * | 5/2014 | Bontempo et al. | 463/17 |

FOREIGN PATENT DOCUMENTS

| | | |
|---|---|---|
| EP | 0101781 A1 | 3/1984 |
| EP | 0856286 A1 | 8/1998 |
| EP | 0993579 A1 | 4/2000 |
| EP | 1690498 A2 | 8/2006 |
| GB | 2133694 A | 8/1984 |
| JP | 07-136173 | 5/1995 |
| JP | 08-071073 | 3/1996 |
| JP | 10277043 A | 10/1998 |
| JP | 11-511366 | 10/1999 |
| JP | 2000007291 A | 1/2000 |
| JP | 2000166930 A | 6/2000 |
| SU | 1482675 A1 | 5/1989 |
| WO | WO-97/10753 A1 | 3/1997 |
| WO | WO-9923935 A1 | 5/1999 |
| WO | WO-0015116 A1 | 3/2000 |
| WO | WO-03/017847 A1 | 3/2003 |
| WO | WO-2004/044632 A1 | 5/2004 |
| WO | WO-2007084641 A2 | 7/2007 |
| WO | WO-2009/090383 A2 | 7/2009 |
| WO | WO-2012/038714 A1 | 3/2012 |

OTHER PUBLICATIONS

Angeli, Markus, "International Search Report", for PCT/GB2009/000097 as mailed Sep. 18, 2009, 6 pages.

Ohtsuka, Toshiya, "Sternum lifting technique for thoracoscopic internal thoracic artery harvest", European Journal of Cardio-Thoracic Surgery, 2005, (5 pages).

Sutherland, et al., U.S. Appl. No. 29/439,486, filed Dec. 11, 2012.

Lamelas, Joseph Intercostal Retractor System, "Miami Method Tailor-Made Exposure Products," Next Generation MICS Instrumentation, 2013, 5 pages.

Cosgrove III, Delos M., et al., "Minimally Invasive Approach for Aortic Valve Operations," The Society of Thoracic Surgeons, 1996, 2 pages.

Gundry, Steven R., et al., "Facile Minimally Invasive Cardiac Surgery via Ministernotomy," presented at Thirty-Third Annual Meeting of the Society of Thoracic Surgeons, Feb. 3-5, 1997, 5 pages.

Plass, Andre, et al., "Aortic Valve Replacement Through a Minimally Invasive Approach: Preoperative Planning, Surgical Technique, and Outcome," The Society of Thoracic Surgeons, 2009, 6 pages.

Murtuza, Bari, et al., "Minimal Access Aortic Valve Replacement: Is It Worth It?," The Society of Thoracic Surgeons, 2008, 11 pages.

Aesculap, "Valve XS: Instruments for Minimally Invasive Valve Surgery," Aesculap Surgical Technologies—Surgical Instruments, 2010, 27 pages.

* cited by examiner

OPTICAL SWITCH

FIELD OF THE INVENTION

The present invention relates to optical switches, especially those used with fibre optic cables. Moreover, the optical switch finds application in various fields, including surgical retractors with lights, for example that found in the disclosure of International Patent Application No PCT/GB2009/000097.

BACKGROUND OF THE INVENTION

Fibre optics are used in a variety of industries including aerospace, telecommunications, lasers and medical devices. A common problem involves switching lights on or off and switching light between paths or combinations of paths. A variety of solutions have been developed to fulfill these requirements including (i) beam splitters, (ii) shuttles, (iii) optical shutters and (iv) variation of the shutter concept, the twisted-nematic liquid crystal shutter.

A beam splitter in its most common form is a cube made from two triangular glass prisms, which are glued together at their base using Canada balsam. The thickness of the resin layer is adjusted such that for a certain wavelength half of the light incident through one "port" i.e. face of the cube is reflected and the other half is transmitted due to frustrated total internal reflection.

A shuttle will usually include an input pipe which moves to align with one of the outputs. A key feature of this switch is that all outputs are exclusive, so it cannot select more than one at a time. Whilst it is possible to create an intermediate position for the shuttle such that it shines light into two outputs, considerable light will be lost at this junction owing to differences in the geometry of the input and outputs. As it stands, there is no "off" position. If one were needed separate from the light source itself, it would either have to separate, or include a dummy switch position.

Common shutter mechanisms include a blade, which may be introduced into a light path to block the transmission of light or rotated out of the light path to allow transmission. The shutter may be spring loaded and attached to a driver such as a rotary solenoid such that the blade moves to the energized position when it receives an operating voltage and returns to its resting position when the voltage is removed. Alternatively, manual operation of the shutter is possible.

The shutter mechanism relies entirely upon a simple mechanical beam blocking effect. It is inefficient as this light is "lost". Furthermore, the "lost" light may be converted to heat, which is undesirable in some applications. Excessive local accumulation of heat can lead to burns in medical device applications where the device is in contact with the patient or user.

Liquid crystal displays provide for another type of shutter: the Twisted-Nematic Liquid Crystal Shutter.

The twisted nematic effect (TN-effect) is the breakthrough that made liquid crystal displays practical in portable devices and allowed them to replace technologies such as light emitting diodes and electroluminescence from most electronics.

TN-cells do not require a current to flow for operation and use low operating voltages suitable for use with batteries. The twisted nematic effect is based on the precisely controlled realignment of liquid crystal molecules between different ordered molecular configurations under the action of an applied electric field. This is achieved with little power consumption and at low operating voltages.

In one example, a TN-cell in the OFF state, i.e., when no electrical field is applied, a twisted configuration of nematic liquid crystal molecules is formed between two glass plates, which are usually separated by several spacers and coated with transparent electrodes.

The electrodes themselves are coated with alignment layers that precisely twist the liquid crystal by 90° when no external field is present. When light shines on the front of the LCD, light with the proper polarization will pass through the first polarizer and into the liquid crystal, where it is rotated by a helical structure. The light is then properly polarized to pass through the second polarizer set at 90° to the first. The light then passes through the back of the cell and the image appears transparent.

In the ON state, i.e., when a field is applied between the two electrodes, the crystal realigns itself with the external field. This "breaks" the careful twist in the crystal and fails to re-orient the polarized light passing through the crystal. In this case the light is blocked by the rear polarizer and the image appears opaque.

The degree of opacity can be controlled by varying the voltage; at voltages near the threshold only some of the crystals will re-align, and the display will be partially transparent, but as the voltage is increased more of the crystals will re-align until it becomes completely "switched". A voltage of about 1 V is required to make the crystal align itself with the field, and no current passes through the crystal itself. Thus the electrical power required for that action is very low.

The obvious advantage such TN-cell shutters have is that they may be operated at very high switching speeds and with low operating voltage. For example switch speed of less than 0.3 milliseconds is typical at room temperature with an applied voltage of only 10V.

Furthermore, activation or switching speed can be enhanced via use of higher operating voltages.

However, the technology has several limitations. Notably, for unpolarised light with 500 nm wavelength (the approximate mid-point of the visible spectrum), transmission of light does not exceed 35% in the ON position, meaning that considerable light is lost. Furthermore, when the device is in the OFF position there is still some light transmitted. Even although the amount of light transmitted is typically less than 0.5% it is not completely blocked as with a purely mechanical shutter mechanism.

Moreover, a long term DC component in the voltage will stimulate impurity ion migration and eventual failure of the device. Therefore such devices have a finite useful lifetime.

Further, caution must be exercised in the handling and cleaning as it is easy to accidently damage the polariser surface or its components, by accidental scratching, use of inappropriate cleaning materials or even simple over-exposure to sunlight.

SUMMARY OF THE INVENTION

According to a first aspect of the present invention there is provided an optical switch comprising a light input, a plurality of light outputs and at least one light pathway, and said light pathway may be selectively moved from a first position, where a light communication path is formed between the light input and a first light output and a second position where a light communication path is formed between the light input and a plurality of light outputs.

Preferably said light pathway is selectively movable to further positions wherein it allows communication between said light input and at least one of said further light outputs.

Preferably there is a plurality of light pathways, either separately or formed with common parts such as a branched arrangement.

Preferably there is a plurality of light inputs, and more preferably said light pathway is selectively movable to further positions wherein it allows communication between at least one of said further light inputs and at least one of said further light outputs.

Preferably said light pathway is selectively movable to an off position wherein light communication between at least one of said light inputs and all of said light outputs is prevented.

Preferably said selective movement of said light pathway is performed by a rotational coupling. It will be appreciated that the light pathway way rotate, or the light pathway may be static and either said light input and/or light output may rotate, or preferably there is provided a rotatable mask between said light input or light output and said light pathway.

Preferably said light pathway is deployed within a pathway housing, said pathway housing having a rotational coupling with respect to either said light input and/or light output.

Preferably said rotational coupling is movable from a first extreme position to a second extreme position, and any point there between, rotation beyond said two extreme being resisted by a stopping mechanism. Preferably said stopping mechanism comprises a protrusion and semi-circular indentation arrangement.

Preferably said rotational coupling includes a plurality of detents, said detents allowing rotation of the rotational coupling to progress in a controlled and step-wise fashion.

Preferably sequential rotation of the rotational coupling results in a predetermined sequential selection of light communication paths being formed between one or more light inputs and one or more light outputs.

Preferably said pathway housing is circular, and more preferably an exterior surface of said pathway housing includes one or more markings indicating the position of said light pathway at different rotational steps.

Preferably said pathway housing is rotatably coupled with said rotatable mask, such that rotation of the pathway housing causes rotation of the rotatable mask.

The rotational coupling may be manually actuated or actuated by some form of motorised actuation means or simply a motor. Programming means may also be included, such as a microchip or microcomputer, so that the optical switch may be programmed to perform a sequence of discrete rotational steps, for uniform or non-uniform time periods.

According to a second aspect of the present invention there is provided a light source including an optical switch according to the first aspect of the present invention.

According to a third aspect of the present invention there is provided a surgical retractor unit including either a light source according to the second aspect of the present invention or an optical switch according to the first aspect of the present invention.

BRIEF DESCRIPTION OF THE DRAWINGS

Reference will now be made, by way of example only, to the accompanying drawings, in which.

DETAILED DESCRIPTION OF THE PREFERRED EMBODIMENTS

Figure 1:
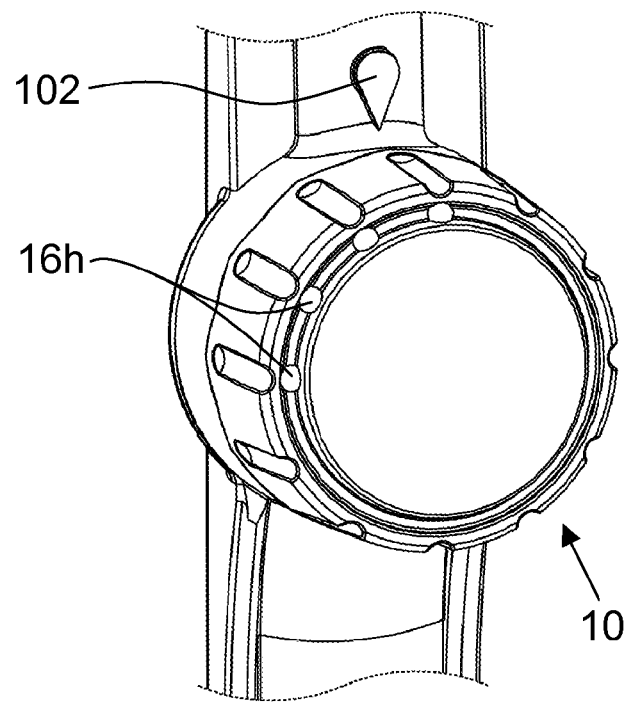
FIG. 1 is an isometric view of an optical switch according to a first aspect of the present invention.
Figure 2:
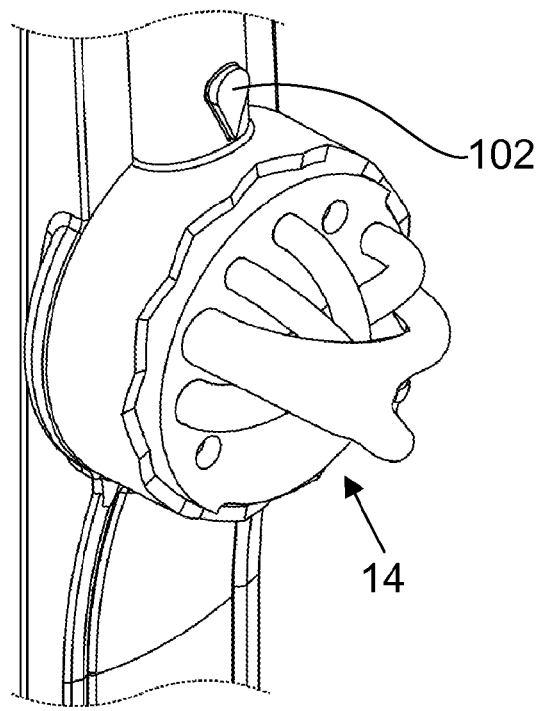
FIG. 2 is an isometric view of the optical switch of FIG. 1 with its housing removed.
Figure 3:
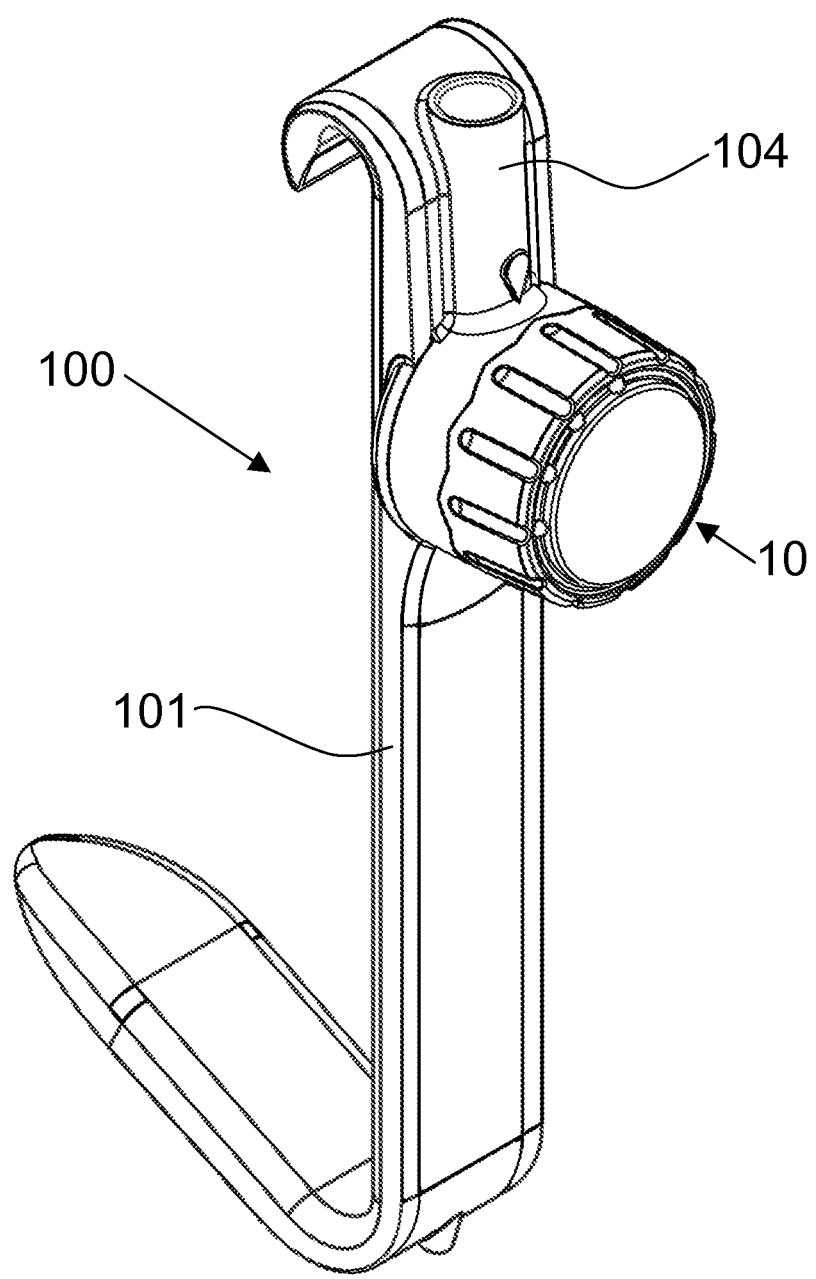
FIG. 3 is an isometric view of the optical switch of FIG. 1 shown mounted on a retractor back assembly of a surgical retractor, according to the third aspect of the present invention.

An optical switch 10 according to a first aspect of the present invention is depicted in FIG. 1. FIG. 3 shows the optical switch as a component part of a surgical retractor 100 according to a third aspect of the present invention.

Figure 4:
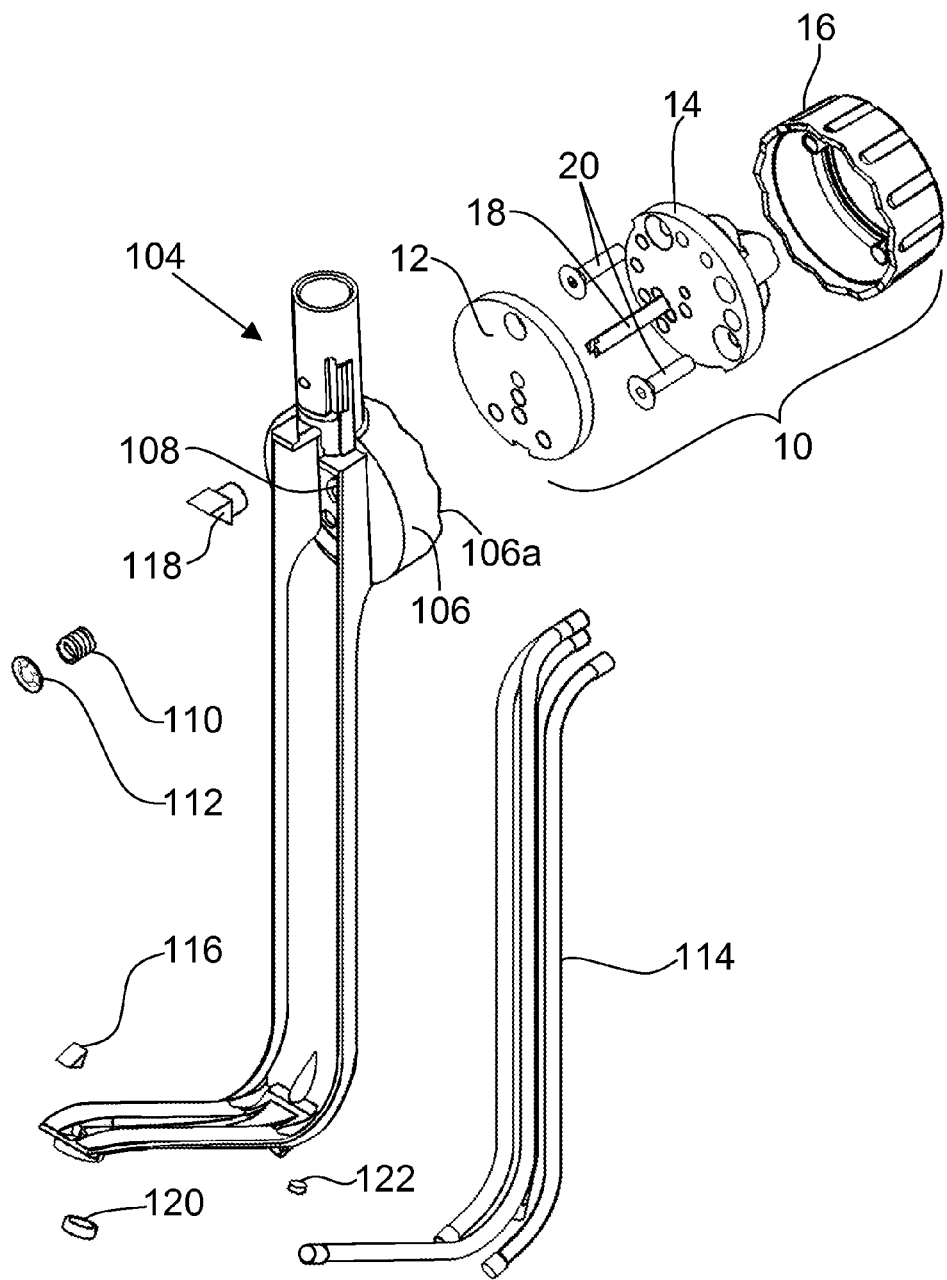
FIG. 4 is a rear isometric exploded view of the retractor back assembly of FIG. 3.
Figure 5:
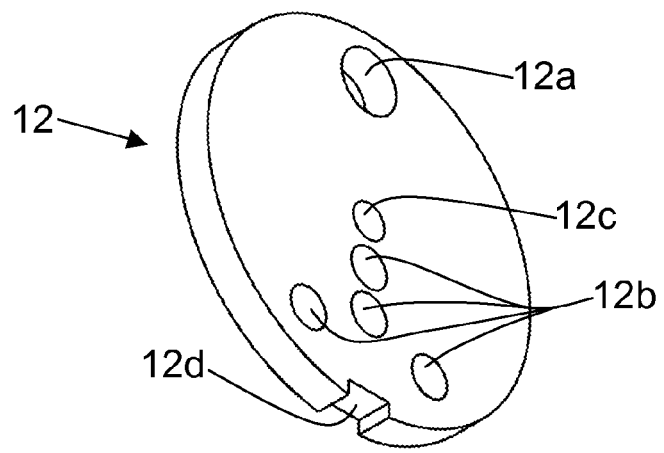
FIG. 5 is an isometric view of a base plate of the optical switch of FIG. 1.
Figure 6:
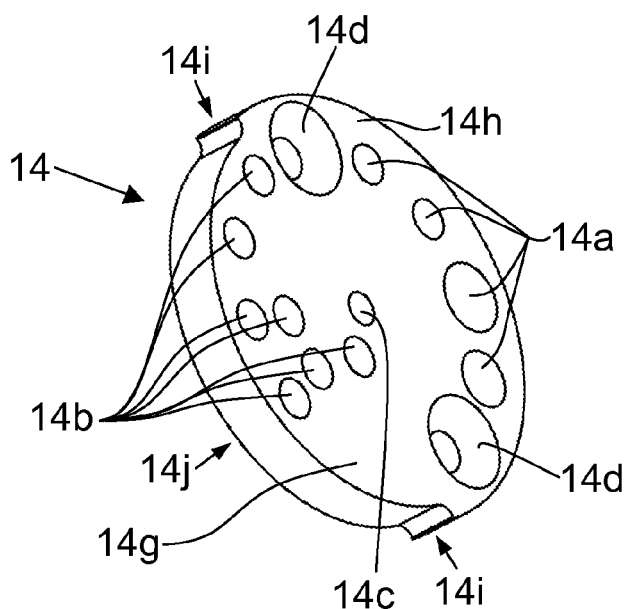
FIGS. 6 & 7 are two isometric views from either side of a light pathway plate of the optical switch of FIG. 1.
Figure 7:
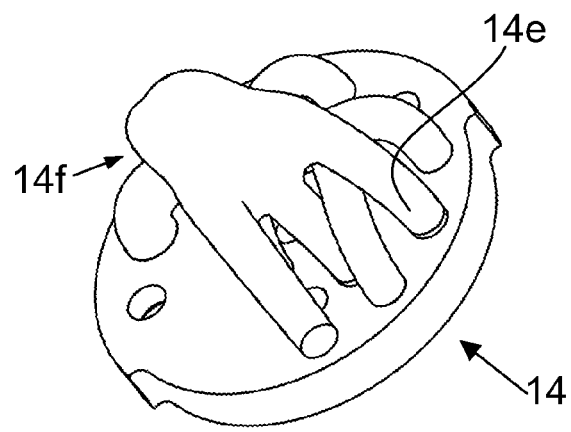
Figure 8:
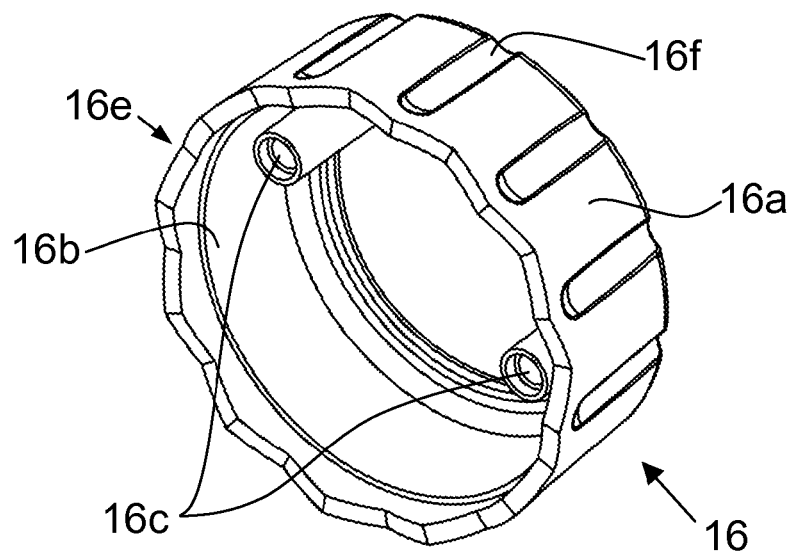
FIGS. 8 & 9 are two views of a housing of the optical switch of FIG. 1.
Figure 9:
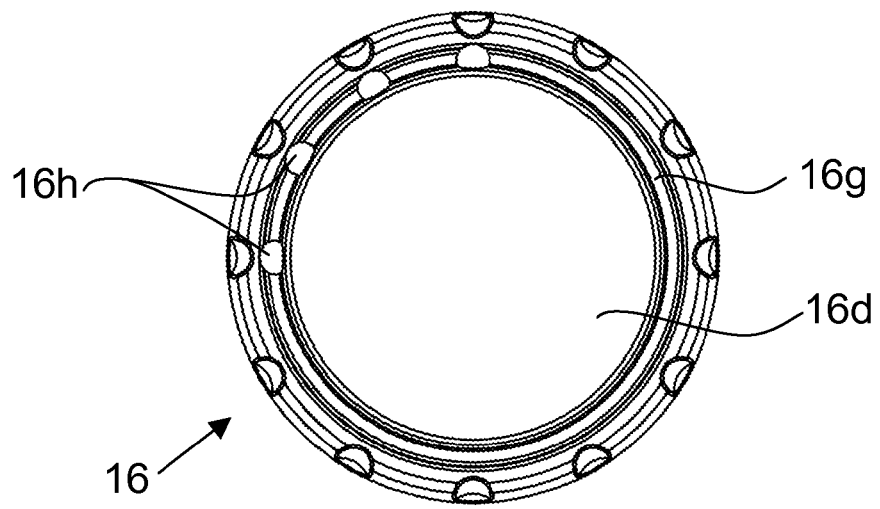

As can be best seen from FIG. 4, the optical switch 10 comprises a base plate 12, a light pathway plate 14 and a housing 16. These three "major" components are attached together via an axle 18 and fixing bolts 20.

The base plate 12 is generally circular, or to be more accurate is a cylinder with its facial diameter far exceeding its height.

The base plate 12 has a number of bores running through it, and these bores define a light input 12a and a plurality of light outputs 12b. Although a single light input 12a is described in the present embodiment, it will be understood that a plurality of light inputs is a possibility, as is a singular light output 12b, or combinations thereof.

There is a base plate central bore 12c which enables assembly and rotation. A further indentation 12d is provided at a location on the circumference of the base plate 12. This allows for the proper orientation of base plate 12 when it cooperates with a corresponding feature on retractor back 104.

The light pathway plate 14 is of a generally similar formation to the base plate 12, being a generally circular plate, and likewise includes various bores running through its depth. Four of these bores define light pathway inputs 14a, whereas several others define light pathway outlets 14b. Further, there is a pathway central bore 14c and two bolt holes 14d which enable assembly and rotation.

One surface of the light pathway plate 14 is a preferably polished smooth, and this surface forms a rotational mating surface with the corresponding surface of the base plate 12.

On the opposite surface is a plurality of light pathways 14e. The light pathways 14e are composed of several strands of fibre optic cable, each forming light pathways between one of the light pathway inputs 14a and one or more of the light pathway outputs 14b. Some light pathways 14e connect from a single light pathway input 14a, to a single light pathway output 14b; whereas some connect from a single light pathway input 14a, to multiple light pathway outputs 14b. Collectively, the light pathways 14e form a pathway bundle 14f.

Although generally circular, the light pathway plate 14 is effectively two semi-circles of material, of two different radii: a smaller radius side 14g and a larger radius side 14h. The two junctions of these two sides around the circumference of the light pathway plate 14, meet at stop lips 14i. Effectively, a stop indentation 14j is formed around a portion of the circumference of the light pathway plate 14.

The stop lips 14i and stop indentation cooperate with a corresponding protrusion (not shown) on whatever member or substrate the optical switch is mounted to, which limits rotation. The corresponding protrusion is mounted through the stop indentation 14*j*, whereby rotation to the extent of the circumference of the stop indentation 14*j* is allowed as the protrusion and stop indentation 14*j* pass over one another. However, at either extreme of allowable rotation, the stop lips 14*i* interfere with the protrusion such that further rotation is resisted. These limits of rotation preferably correspond to OFF positions of the optical switch i.e. where light entering the device is not presented with a light pathway to move through the optical switch 10.

The housing 16 is cup-shaped and comprises an outer surface 16*a*, an inner surface 16*b* and two housing sockets 16*c*. The outer surface 16*a* is itself composed of two discrete surfaces: a fascia 16*d* and a side-wall 16*e*. To aid operation, ergonomically knurled grips 16*f* are indented on the side-wall 16*e*. The distal edge of the side-wall 16*e* from the fascia 16*d* is formed in the pattern of multiple interconnecting chevrons, so that a "zig-zag" pattern is formed i.e. the relative height of the projection of the side-wall 16*e* away from the fascia 16*d* varies in a regular pattern from a minimum to a maximum.

The fascia 16*d* includes an indented rim 16*g* adjacent the outer circumference of the fascia. Within the indented rim 16*g* are four indicator knobs 16*h*. The indicator knobs 16*h* act as gauges to determine the degree of rotation of the switch 10, and act in conjunction with some form of corresponding pointer, in this case an arrow 102 provided on retractor back 104. This provides a simple passive scale, but may be replaced with a more active device, such as lights or the like.

The assembly of optical switch 10 can be best seen in FIG. 4. The light pathway plate 14 is sandwiched between the base plate 12 and the housing 16. The axle 18 runs through the light pathway plate 14 and base plate 12, whilst the bolts 20 connect the light pathway plate 14 to the housing 16. Thus, the base plate 12 and the combination of light pathway plate 14 and housing 16 may rotate with respect to one another.

The optical switch 10 is attached to a surgical retractor having lights, similar to that described in International Patent Application No. PCT/GB2009/000097.

The surgical retractor has a main body 101 and a retractor back 104. The retractor back 104 is a substantially plastic component which acts as a main structural component for the surgical retractor. The retractor back 104 includes within it a socket 106. The socket 106 is adapted to receive the optical switch 10, via the base plate 12. The side-wall 106*a* of the socket 106 has a similar interconnecting chevron-like profile to that of the side-wall 16*e* of the housing 16. These cooperating surfaces ensure that rotation of the light pathway plate 14/housing 16 assembly (which are locked and therefore rotate together) relative to the base plate 12/retractor back 104 proceeds in a controllable and step-wise fashion.

The axle 18 connects through an aperture 108 which passes through the retractor back 104. The axle is retained using a spring 110 and a locking clip 112.

A protrusion (not shown) projects from the retractor back 104 to limit rotation of the light pathway plate 14 by the mechanism described above.

Optical fibres 114 are provided which channel light away from, the optical switch 10. Light is provided by an external light source (not shown) via a light guide (not shown) which attaches to the top of the retractor back 104. Prisms 116,118 and lenses 120,122 are also provided for further control of light that passes into and through the optical switch 10, and out of the surgical retractor via optical fibres 114. Inlet prism 118 receives light from the external light source (not shown) and bends this through 90° before entry into a light input 12*a*.

In use, light from an external source (not shown) is directed into the optical switch 10, passing through the base plate 12 via a light input 12*a*. The optical switch 10 will have a particular setting, defined by the relative rotation of the light pathway plate 14/housing 16 assembly with respect to the base plate 12/retractor back 104.

Light continues through the optical switch 10 passing through a light pathway input 14*a*, into one or more light pathways 14*e* defined as part of a pathway bundle 14*f* to the light pathway output 14*b* and on through to a light output or light outputs 12*b*. Finally, the light passes back through one or more of the optical fibres 114 and out of the device and onto, for example, a lighting rig (not shown) for illuminating part of a patient (not shown). In this particular example, it will be assumed that the optical switch 10 is selected in a switching position to receive a single light input and provide a single light output, for example providing light to a single external light source.

The user, who may be a surgeon or other medical professional in an operating theatre, may then rotate the light pathway plate 14/housing 16 assembly with respect to the base plate 12/retractor back 104 to a second switching position.

In this situation, a different a light pathway input 14*a* is presented to the light input 12*a*, and consequently the light passes into a different light pathway 14*e* defined as a further part of the pathway bundle 14*f*, and onto a different light pathway output or outputs 14*b*, and further on through to a different light output or light outputs 12*b*.

In this second example, it will be assumed that the second light pathway branches into two separate light pathways on the fibre bundle 14*e*, and onto two light pathway outputs 14*b*, and further on through two light outputs 12*b*. Thus, two beams of light exit through to the optical fibres 114 and may be channeled, for example, to two separate external light sources. Thus the user may select to illuminate two separate portions of a patient, or simply provide a more diffuse light source over a greater area. It will be understood that further selections are possible, such as branching from one light source to three or more, or indeed from several light sources to a single, or indeed the same or different amounts of light outputs. For example, during an operation which comprises three or more steps, the specific lighting requirements may be set within three or more selections preselected within the optical switch. Thus, the user may start the operation with the first selection which, for example, may provide optical illumination for a first surgical task such as entering a chest cavity, moving to the second selection which, for example, may provide optical illumination for a second surgical task such as operating on a particular human organ or major blood vessel within the chest cavity, and onto the third selection which, for example, may provide optical illumination for a third surgical task such as operating inside a human organ or major blood vessel.

Furthermore, programming means may be used to allow for controlled and automatic rotation of the optical switch 10 to different switch positions in a particular programmed sequence, or indeed there may be a remote control device, voice activation, ambient light sensor, or other form of control means adapted to move to different switching positions.

Although described with respect to the medical field, it will be apparent that the optical switch 10 may find application in other fields.

It should be further noted that various adjustments and reconfigurations are possible to the illustrated embodiment as described above within the scope of the invention as will be apparent to those skilled in the art.

The invention claimed is:

1. An optical switch comprising:
a base plate comprising a first plurality of bores for light input and light output; and
a light pathway plate comprising:
a second plurality of bores defining a plurality of light pathway inputs and a plurality of light pathway outputs;
a first surface on which first surface a plurality of light pathways are formed between a light pathway input of the plurality of light pathway inputs and at least one light pathway output of the plurality of light pathway outputs, the plurality of light pathways being formed in an optical cable bundle on the light pathway plate;
a second surface opposite the first surface for cooperation with the base plate; and
wherein said light pathway plate is selectively movable with respect to the base plate from a first position where a first light communication path connects a light input and a first light output and a second position where a second light communication path connects the light input and at least one further light output.

2. The optical switch as claimed in claim 1, wherein in the first position the light input is connectable with a plurality of light outputs.

3. The optical switch as claimed in claim 1, comprising a plurality of light inputs.

4. The optical switch as claimed in claim 3, wherein said light pathway plate is selectively movable to further positions wherein said light pathway plate allows communication between at least one of said plurality of light inputs and at least one of said further light outputs.

5. The optical switch as claimed in claim 1, wherein said light pathway is selectively movable to an off position wherein light communication between at least one of said light inputs and all of said light outputs is prevented.

6. The optical switch as claimed in claim 1, wherein selective movement of said light pathway plate is performed by a rotational coupling.

7. The optical switch as claimed in claim 6, wherein the rotational coupling is manually actuated.

8. The optical switch as claimed in claim 6, wherein the rotational coupling is actuated by a motor.

9. The optical switch as claimed in claim 6, including a programmable device, said programmable device being programmable to perform a sequence of discrete rotational steps, for uniform or non-uniform time periods.

10. The optical switch as claimed in claim 1, wherein there is provided a rotatable mask between said light pathway plate and at least one of said light input and light outputs.

11. The optical switch as claimed in claim 10, wherein said light pathway is deployed within a pathway housing and said pathway housing is rotatably coupled with said rotatable mask, such that rotation of the pathway housing causes rotation of the rotatable mask.

12. The optical switch as claimed in claim 1, wherein said light pathway is deployed within a pathway housing, said pathway housing having a rotational coupling with respect to at least one of said light input and light output.

13. The optical switch as claimed in claim 12, wherein said rotational coupling is movable from a first extreme position to a second extreme position, and any point there between, rotation beyond said two extremes being resisted by a stopping mechanism.

14. The optical switch as claimed in claim 13, wherein said stopping mechanism comprises a protrusion and semi-circular indentation arrangement.

15. The optical switch as claimed in claim 13, wherein said rotational coupling includes a plurality of detents, said detents allowing rotation of the rotational coupling to progress in a controlled and step-wise fashion.

16. The optical switch as claimed in claim 13, wherein rotation of the rotational coupling sequentially results in a predetermined sequential selection of light communication paths being formed between one or more light inputs and one or more light outputs.

17. The optical switch as claimed in claim 12, wherein said pathway housing is circular.

18. The optical switch as claimed in claim 17, wherein an exterior surface of said pathway housing includes one or more markings indicating the position of said light pathway at different rotational steps.

19. The optical switch as claimed in claim 1, wherein the optical switch comprises a base plate, a light pathway plate and a housing mounted for rotation upon an axle the housing being cup-shaped with a crenellated edge of side wall for engaging a corresponding edge of a mounting socket.

20. The optical switch as claimed in claim 1, wherein the light pathway plate is generally circular and has two circumferential side portions defined by different radii to form relative to one another, a smaller radius side and a larger radius side, wherein two junctions of these two side portions define stop lips configured to cooperate with a stop member to limit a range of rotation of the light pathway plate.

21. The optical switch as claimed in claim 1, wherein the housing comprises a fascia including an indented rim adjacent the outer circumference of the fascia including mutually spaced indicator knobs serving to determine the degree of rotation of the switch relative to a reference point beyond the housing.

22. A light source including the optical switch as claimed in claim 1.

23. A surgical retractor unit including the optical switch as claimed in claim 11.

24. The optical switch as claimed in claim 1, wherein in the second position, the light input is connectable with a plurality of light outputs.

25. The optical switch as claimed in claim 1, wherein said light pathway is selectively movable with respect to the base plate from the first position or the second position to a third position where a third light communication path connects the light input and a third light output.

26. The optical switch as claimed in claim 25, wherein said light pathway plate is selectively movable with respect to the base plate to at least one further position wherein further light communication paths connect the light input and at least one further light output.

* * * * *